(12) United States Patent
Eklund et al.

(10) Patent No.: US 6,375,934 B1
(45) Date of Patent: Apr. 23, 2002

(54) SYSTEM FOR OPTIMIZED FORMATION OF FLUORAPATITE IN TEETH

(75) Inventors: Bengt Eklund, Norrkoping; Sune Wikner, Umea, both of (SE)

(73) Assignee: Care Aid 2000 AB, Norrkoping (SE)

( * ) Notice: Subject to any disclaimer, the term of this patent is extended or adjusted under 35 U.S.C. 154(b) by 0 days.

(21) Appl. No.: 09/700,223

(22) PCT Filed: May 17, 1999

(86) PCT No.: PCT/SE99/00831
  § 371 Date: Nov. 13, 2000
  § 102(e) Date: Nov. 13, 2000

(87) PCT Pub. No.: WO99/59496
  PCT Pub. Date: Nov. 25, 1999

(30) Foreign Application Priority Data
May 18, 1998 (SE) .............................................. 9801765

(51) Int. Cl.$^7$ ................................................. A61K 7/16
(52) U.S. Cl. .................... 424/52; 433/217.1; 433/228.1
(58) Field of Search ............................... 424/49, 58, 52

(56) References Cited

U.S. PATENT DOCUMENTS

| | | | | |
|---|---|---|---|---|
| 1,112,180 A | * | 9/1914 | Westenfelter | 424/49 |
| 1,717,723 A | * | 6/1929 | McCall | 424/49 |
| 2,151,495 A | * | 9/1939 | Bender | 167/93 |
| 3,332,743 A | | 7/1967 | Green | 23/230 |
| 3,507,269 A | * | 4/1970 | Berry | 128/2 |
| 3,746,624 A | * | 7/1973 | Hoerman et al. | 195/100 |
| 4,048,300 A | * | 9/1977 | Tomlinson et al. | 424/52 |
| 4,108,980 A | | 8/1978 | Duff | |
| 4,150,106 A | * | 4/1979 | Assal et al. | 424/49 |
| 4,223,003 A | * | 9/1980 | Scheller | 424/49 |
| 4,342,741 A | * | 8/1982 | Aoki | 424/57 |
| 4,359,455 A | * | 11/1982 | Nakamura et al. | 435/4 |
| 4,397,944 A | * | 8/1983 | Komura et al. | 435/4 |
| 4,568,534 A | * | 2/1986 | Steir et al. | 424/49 |
| 4,582,795 A | * | 4/1986 | Shibuya et al. | 435/34 |

FOREIGN PATENT DOCUMENTS

| | | | |
|---|---|---|---|
| FR | 944506 | * | 4/1949 |
| GB | 1289323 | * | 1/1969 |
| GB | 2112642 | * | 7/1983 |
| JP | 56058663 | | 5/1981 |
| WO | 96/29047 | * | 9/1996 |

OTHER PUBLICATIONS

Merck Index 12$^{th}$ Ed Misc —58–59 Table I—Indicators pH Values, 1996.*

* cited by examiner

*Primary Examiner*—Shep K. Rose
(74) *Attorney, Agent, or Firm*—Merchant & Gould P.C.

(57) ABSTRACT

The invention consists of a system comprising a measuring device of shape adapted to the tooth, which with yellow, green and blue color grades the current pH value in the patient's tooth film and in which the green color indicates the optimum pH value for the formation of caries-counteracting fluorapatite. Three types of color-matching tubes of toothpaste have compositions that contain fluoride and center the pH values of the tooth films on the green level. The system's measuring device shows by colorimetric means which toothpaste will at that precise time best promote the formation of fluorapatite in each of the three pH groups form which the device selects.

18 Claims, 4 Drawing Sheets

Yellow test result

Green test result

Blue test result

Figure 1A:
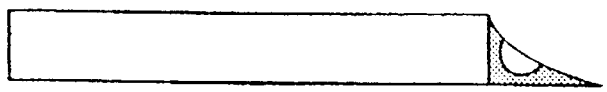

■ Blue test result
▒ Green test result
☐ Yellow test result

SYSTEM FOR OPTIMIZED FORMATION OF FLUORAPATITE IN TEETH

Persons who are prone to dental caries are inadequately served by today's preventive dental care. Lack of educational awareness in dental care and lack of odontological awareness in education has meant that there are insufficient aids and working methods to help these persons effectively.

The invention relates to a system that solves the problem according to the pre-characterising part of claim 1.

Dental caries is the world's most common multifactoral disease but also one that it is possible to avoid by means of personal care measures for those who have adequate knowledge of the disease process and their own susceptibility to disease at a given time. This is because the risk of caries varies between individuals and in the individual over time. There is therefore no single method of prevention that will help all individuals every time.

If dental care personnel had the knowledge, capability and incentive to teach the patient how to proceed at any given time in order to counteract caries, the need for dentists would be drastically reduced. A corresponding effect would be achieved if skilled teachers had the odontological training that is required. So the aids which the dental hygienist needs in order to train patients are not developed for this. The lack of educationally sound aids and working methods is a problem in dental care.

It is well known that fluoride prevents dental caries and that the most important mechanism is the formation of fluorapatite on the tooth surface in connection with a reduction of the pH level to a given interval. It is also known that fluoride does not have an adequate protective effect in persons highly susceptible to caries, despite the fact that a large number of studies have been carried out with systems of fluoride administration currently in use. The most important source of fluoride is reckoned to be toothpaste.

That fluoride treatments fail is due to the fact that the dental hygienist does not take into consideration that dental caries is a multifactoral disease. It is not sufficient, as at present, to try to solve the problem of caries simply with large doses of fluoride. A factor of at least equal importance is the pH-value in the films on the tooth surface.

After eating carbohydrates the caries process causes a reduction of the pH value of the tooth films from a normal value of approximately 7.0–7.5. After a time that varies according to the individual the pH value rises again to the normal value. The curve described by the pH value during this time is known as Stephan's curve. Important factors that affect its appearance are partly the concentration of acid-producing microorganisms in the tooth films, including streptococci mutans, which end to reduce the pH value. Buffer substances, which are present in normal saliva. endeavour to counteract the reduction and to increase the pH value after a reduction. The most important buffering systems are founded on the presence of bicarbonates and phosphates in the saliva, but proteins, urea and mucoid substances have buffering characteristics.

An individual may have a number of combinations of bacteria content and buffering capacity and many Stephan curves with different appearance therefore exist. Extreme variants include, on the one hand, a pH reduction from the normal value of 7.0, by about one pH unit for a few minutes, and on the other a large reduction to values of less than 4.0 for up to two hours. Owing to a number of circumstances all these variants can, in theory, occur in each individual from time to time.

Despite the great significance of buffering for the appearance of the Stephan curve, clinical studies have only been able to show a slightly negative correlation between the buffering capacity of the saliva and caries in a normal population. The reason is that there are many other factors that affect the development of caries, among other things the presence of fluoride, good oral hygiene and good discipline with regard to sugar, all of which reduce the strength of the connection. In clinical studies the connection was so weak that simply measuring the strength of the buffering is not regarded as adequate for assessing the risk of caries in an individual. In persons with a high bacteria content on the tooth surface the correlation is greater and is due to the fact that many of these persons have a large pH reduction after eating, which increases the prophylactic importance of the pH-increasing buffering.

It is generally assumed that the correlation is linear and that persons with the highest buffering capacity should run the least risk of caries. In one (unpublished) clinical study of 96 teenagers with high acid-producing content of streptococci mutans in the saliva we found, however, that persons with medium buffering had least caries of all, including those who had better buffering (Table 1).

TABLE 1

Number of tooth surfaces with caries in 96 14-year olds with more than 1 million CFU Streptococci mutans per ml saliva. The buffering capacity (final pH) is registered with Dentobuff.

| Final pH | DS | SD |
| --- | --- | --- |
| <4.5 | 6.6*** | 4.9 |
| 4.5–5.5 | 2.9* | 2.8 |
| >5.5 | 4.6 | 3.1 |

*indicates $P < 0.05$
***$P < 0.001$

The high standard deviations indicate that a few individuals had developed great caries attack in each group. Note that this is a cross-sectional study and the result shows the accumulated quantity of caries attack over several years. It is highly probable that the buffering capacity of many participants has changed during the period (Table 2), which explains why certain persons with high buffering values at present (>5.5) have a large amount of caries damage. All those taking part have been exposed to fluoride rinses every 14th day from the age of 7 and have used fluoride toothpaste regularly.

These observations indicate that the intermediate group run a lower risk of caries than the group with an inferior or superior buffering capacity in a material that is exposed to fluoride.

TABLE 2

Percentage distribution of high and low buffering values on three occasions over 18 months in 255 school children with high bacteria values in the saliva (unpublished)

| | Test intervals | | |
| --- | --- | --- | --- |
| | Start | 6 months | 18 months |
| Buffering capacity | % | % | % |
| Low (<5) | 69.7 | 34.5 | 62.0 |
| High | 30.3 | 65.5 | 38.0 |

Table 2 shows that the proportion of persons who had low buffering capacity was halved during the first six months. After a further year the proportion was the same at the start.

In the light of this there are good reasons to assume that it is a combination of fluoride and exactly the right buffering capacity which gave the intermediate group in Table 1 less caries than the high-buffering group.

From a practical point of view the result in Table 1 indicates that the risk of caries should be reduced if the content of buffering substances in the low buffering group could be increased, whilst a lowering of this in the high-buffering group should reduce caries in that group.

Fluoride Reduces the Critical pH Level

If there is fluoride deficiency in the mouth, the tooth enamel looses minerals when the pH value has dropped to less than 5.5 after eating. A low-buffering person very often has a lower pH value after eating than a person with higher buffering. If fluoride is present the critical limit is reduced to 4.5. In the pH interval 4.5–5.5 the enamel is certainly demineralised first, but afterwards a precipitation of fluorapatite occurs, which compensates for the mineral loss and forms a surface that has high resistance to the low pH values.

Moderate pH Fall Promotes Formation of Fluoranatite

Above pH 5.5 the formation of fluorapatite is a slow process. pH is often at this level in persons who belong to the high buffering group. If the pH on their tooth surfaces is reduced from 7.0 to 5.0, the rate of formation of fluorapatite rises 20 times (ref. 2).

Large pH Fall Prevents Formation of Fluorapatite

If the pH falls below 4.5 a constant mineral loss occurs and fluorapatite is not formed without the presence of a very high fluoride concentration and the longer this low pH value exists, the greater the mineral loss becomes. Persons in the low-buffering group in our study develop low pH values more frequently than the other groups, which explains why they get so much caries.

It can be demonstrated that, after eating, certain persons develop pH values as low as or lower than 4.0 in tooth films (ref. 3). In some of these persons the pH value returns to the normal 7.0 with a few minutes (ref. 4). whilst others may have a mineral-dissolving low pH value for up to two hours (ref. 3). When the pH value increases from 4.0 to 5.0, the mineral loss is greatly reduced even at very low fluoride concentrations (ref. 1). For persons who usually develop low pH values in tooth films after eating, such a raising of the pH value following each consumption of food gives a good fluoride protection with a significantly lower quantity of fluoride than is required if fluoride alone is used, without pH adjustment. According to ten Cate & Duijsters 5 ppm should be required at pH 4.0, but at pH 5.0 only 0.05 ppm is required in order to achieve the same effect, that is to say raising the pH value by one unit should reduce the fluoride requirement to one hundredth.

In the light of this it is probable that the intermediate-buffering group in our study (Table 1) forms fluorapatite better than the high-buffering group and considerably better than the low-buffering group, due to the fact that the optimum pH value for apatite formation occurs more often than in other groups.

pH Correction Required

In the light of this, persons who develop pH values that lie outside the interval 4.4–5.5 ought to be treated with orally administered substances that bring the pH value into this interval, increasing the formation of fluorapatite and reducing caries.

Identification Problem

The problem is to identify these persons. None of the tests that are currently used manage this. Although the buffering capacity of the saliva provides a guide, it tells us nothing about the occurrence of streptococci mutans, which has an influence on the appearance of the Stephan's curve. Furthermore it provides no information on the buffering, which occurs in the tooth films. Nor does the occurrence of streptococci mutans provide adequate information, since its tells us nothing about the buffering. Even a combination of these two tests does not provide sufficiently accurate information on what happens in the plaque after eating.

pH-influencing Toothpastes

In Sweden toothpastes with a pH value of 5.5 are to be found. In other countries there are quite a few with even lower pH. A low pH value in toothpaste is reckoned to produce a suitable lowering of a high pH value in tooth films and thereby to increase the formation of fluorapatite. The idea is logical but assumes that the pH-reducing toothpaste is not used by persons prone to caries, who have just consumed carbohydrates. In these people the toothpaste rather tends to reinforce the normal pH reduction that occurs after eating and risks reducing pH too far, that is to say below 4.5 over a prolonged period, when mineral is lost without any formation of fluorapatite to compensate. In practice, therefore, acid toothpastes increase the risk of caries in these persons. Acid toothpaste must only be used by persons who are shown to experience a large or short-term pH fall after eating, for example high-buffering persons.

There is a problem that persons who develop low pH levels after eating sometimes use toothpaste with a low pH value.

Some Toothpastes Have a pH Value That Is Higher Than the Normal pH Value of the Saliva A high pH value in toothpaste is reckoned to produce a rise in a pH value that is too low, thereby interrupting the caries process and promoting the formation of fluorapatite, but if it is used by persons who have an insignificant or moderate fall in the pH value after eating there is a great risk that the pH value will be increased to a level at which only insignificant quantities of fluorapatite are formed, for example the high-buffering group in our study. Due to the small quantity of acid-resistant fluorapatite their preparedness for changes in the risk of caries is therefore poor. This does not matter as long as a high pH level is maintained after eating. But the saliva mechanisms that affect the appearance of the Stephan's curve are unfortunately changed over time in certain individuals (Table 2). This can means that persons who once had optimum protection against caries owing to the formation of fluorapatite may later experience a pH reduction that goes below 4.5, thereby rapidly increasing the development of caries.

A high pH value in toothpaste must therefore only be used by persons who are shown to experience a large, long-lasting fall in pH level after eating.

There is a problem that persons who for a short time return to a high pH level after eating sometimes use toothpaste with a high pH value.

Acid and basic toothpastes on sale do not inform the public of these risks. Another deficiency of these toothpastes is that the purchaser does not know whether the pH change they initiate leads to optimum conditions for the formation of fluorapatite. There is no indication, for example, whether one or two cm are to be used. Is one to se a single or a double dose of the substance that affects the pH level? The wrong choice can lead to a minimal formation of fluorapatite.

The reason for these deficiencies is that there is no practical measuring technique that shows the individual which toothpaste gives the best fluorapatite production and hence the optimum protection against caries in a particular case. This is a problem.

An American patent filed in 1978 (U.S. Pat. No. 4,108, 980) describes a pH reducing composition with fluoride and a pH-increasing composition. The patent does not indicate, however, on which patients these compositions are to be used or how these are to be identified. The patent claim only covers the reduction of a pH level that is too high with a view to increasing the formation of fluorapatite. The method and the pharmaceutical preparations can not be used in the manner prescribed for persons who, when being treated, have a low pH value on the tooth surface. This would then, on the one hand, counteract the formation of fluorapatite, and on the other would increase the demineralisation, both of which are contrary to the aim of the patent's application. Nor can the pharmaceutical preparations specified by the patent be used by the general public.

The object of the invention is to solve the above-mentioned problem. The solution provides dental care personnel with an educationally well though-out system of working with adequate aids, which in turn helps the patients firstly to understand their risk of caries and secondly to take the measure that is currently required in order to prevent caries.

The invention comprises an educational system containing a device which with yellow, green or blue colour graduates the current pH level in the patient's tooth film where the green colour indicates the optimum pH level for the formation of caries-counteracting fluorapatite. The systems colour-matching interpretation template for dentists and colour-matching diagnostic chart with explanatory text are aids for training the patient. Three types of colour-matching toothpaste tubes have compositions that centre the pH level of the tooth films on the green level. The system's measuring device shows in colorimetric form which toothpaste at that precise time best counteracts caries in each of the three pH groups.

Figure 1B:
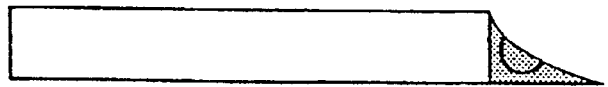
Figure 1C:
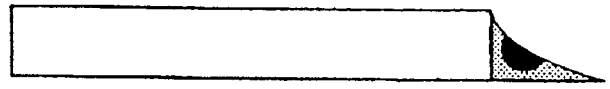

One embodiment of the measuring, device according to the invention is shown in FIGS. 1a–1c. One end has a green-coloured reagent part, which contains desiccated 0.09 per cent alcohol solutions of bromocresol blue and bromothymol blue. One side of the reagent part has the same profile as a toboggan-run.

This part is intended to be inserted between two teeth that are in contact with one another, with the curved part of the device against the point of contact of the teeth. Its curvature is designed so that the device will fit most teeth and touch the point of contact in the teeth interstice.

The device functions as follows. The test subject consumes some product containing carbohydrate or a five per cent sugar solution is dripped over the contact point that is to be tested. After approximately 20 minutes the device is inserted between the teeth as far as it will go and held in place for up to one minute. The device is removed and the colour change occurring is registered on the reagent field.

If the colour is yellow (FIG. 1a) this means that the exposure to sugar has caused a pH fall that is so profound and persists for so long that the teeth are loosing mineral without this loss being compensated for by newly formed fluorapatite. With this result, a toothpaste should be used after eating that is capable of increasing the pH value to the optimum level for formation of fluorapatite.

If the colour on the reagent field is green (FIG. 1b), the formation of fluorapatite is in progress since the pH value is an optimum one. A suitable toothpaste is then one that neither raises nor reduces the pH level but rather preserves the current one.

If the colour is blue (FIG. 1c), the buffering substances of the saliva and the tooth films have already raised the pH to the level at which no fluorapatite is formed. A suitable toothpaste is one that reduces the pH value to the optimum level for the formation of fluorapatite.

Suitable Toothpastes

None of the toothpastes on the market has been adapted with the deliberate aim of adjusting the pH level to the interval at which the optimum formation of fluorapatite occurs. It may be that by chance one of them may be quite suitable for the user, but nobody has demonstrated this. We have therefore produced toothpastes with such characteristics.

The Toothpaste Functions in the Following Way

Figure 2A:
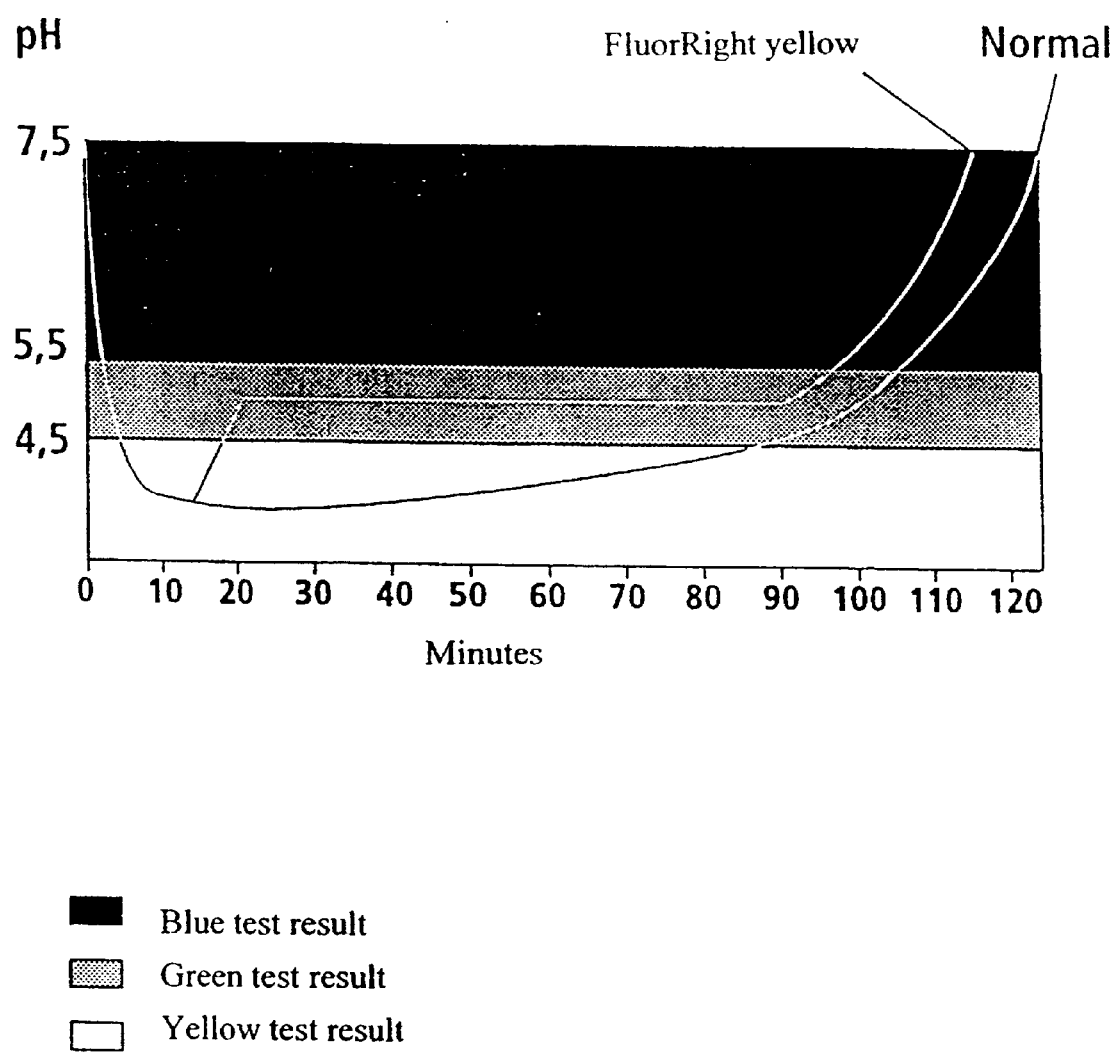

A yellow-coloured toothpaste has a pH value of 8.0 and one embodiment contains the pH-increasing substances $Na_2HPO$ (3.43 g), $NaH_2PO_4xH_2O$ (3.31 g), $NaHCO_3$ (3.22 g), $(NaPO_3)_6$ (1.24 g) or a total of 11.2 g per 100 g of toothpaste and is intended for persons who obtain a yellow test result after exposure to sugar. In repeated tests in our laboratory we have shown that a yellow result on the reagent field is immediately changed to green when yellow toothpaste is applied. This means that the toothpaste increases the pH value to the level at which optimum fluorapatite formation occurs (FIG. 2a).

Figure 2B:
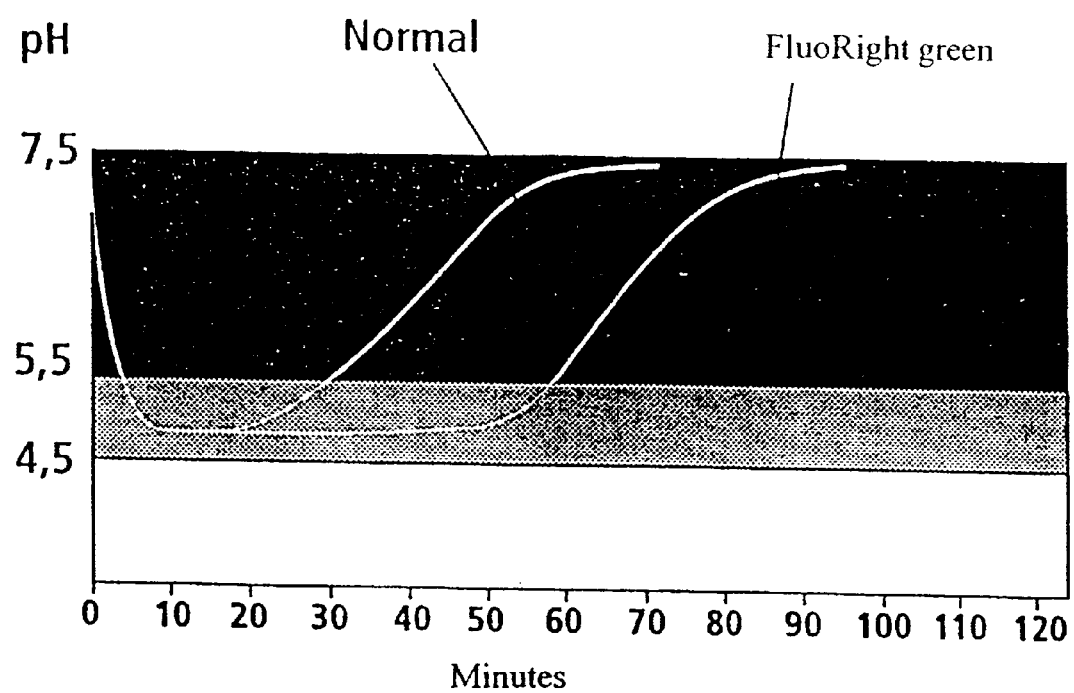

A green toothpaste has a pH value of 5.0 and in our tests we have shown that it does not affect the original colour of the reagent field. This means that the toothpaste supplies substances with the same pH value as are currently present at the point of contact between the teeth and prolongs the time for this pH value (FIG. 2b).

Figure 2C:
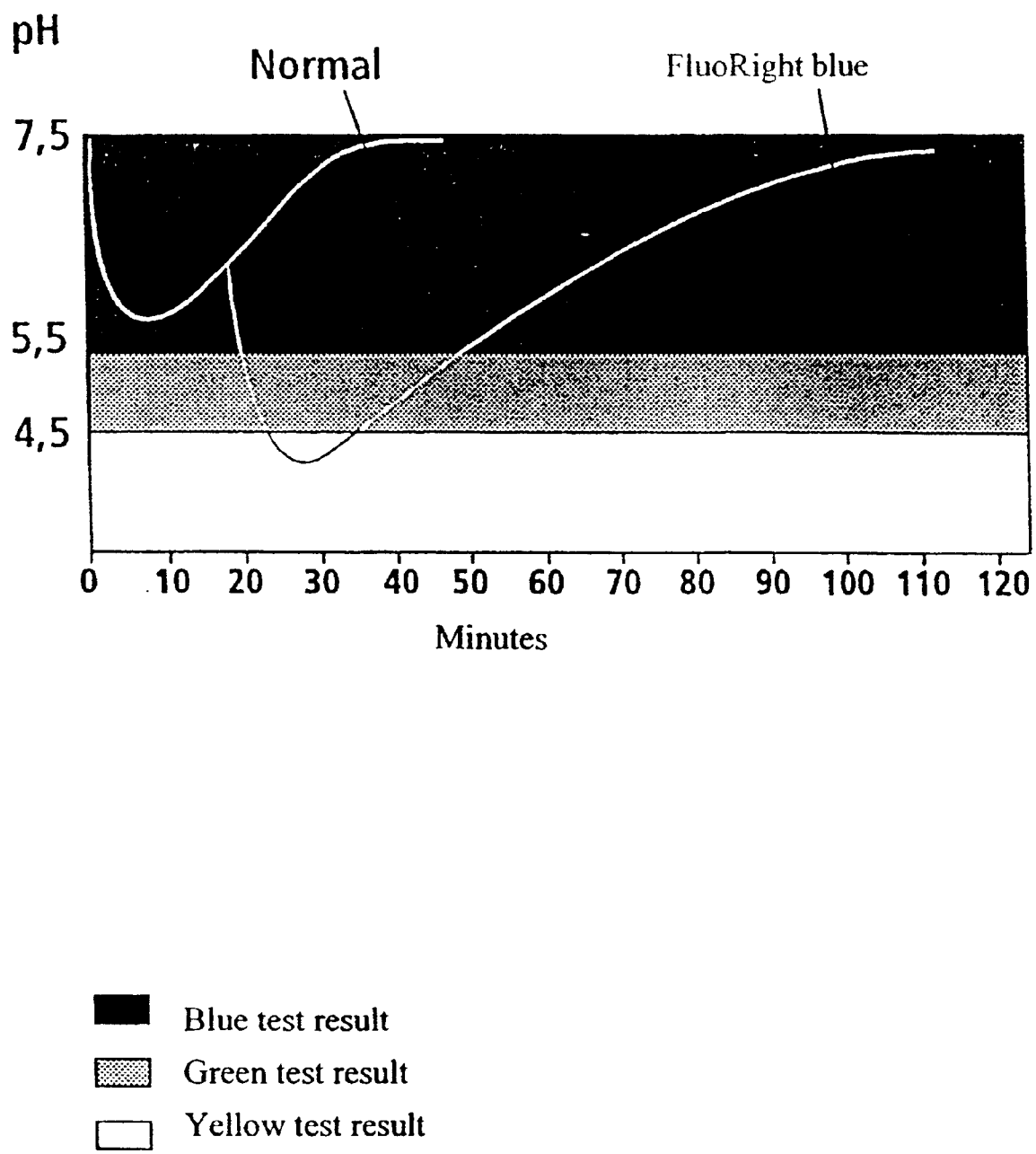

A blue toothpaste has a pH value of 4.0 and contains pH-reducing substances such as citric acid. This is intended for the blue test group and our tests show that it reduces the pH value from the blue to the green test level, that is the level at which optimum fluorapatite formation occurs (FIG. 2c).

The quantity of citric acid used in order to give green and blue toothpaste the right pH characteristics varies between 0.3–0.9% and is dependent on the pH value of other ingredients in each batch. Corresponding variation may also occur in the manufacture of yellow toothpaste, which affects the need for bicarbonate in order to provide the required characteristics.

At pH 4.0 100 times more fluoride is required in order to prevent mineral loss than at pH 5.0. With access to the result from the measuring device and toothpastes that adjust the pH value to a narrow interval around 5.0 the fluoride content of the toothpastes can be kept at a much lower level (0.01–0.001% F.) than ordinary toothpastes.

Persons with high susceptibility to caries cause major economic problems for themselves and for the community. For some decades researchers have searched high and low for preventive working methods that can be used in the defined group. There has hitherto been a lack of data showing that fluoride treatment helps (ref. 5), but despite this dental care personnel have persisted in trying to solve the problem simply by high doses of fluoride.

Not one researcher who published key data on the pH-dependency of fluorapatite has been able to demonstrate a practical working method. For this reason putting together our method of solving the problem cannot be deemed obvious to the person skilled in the art. The invention is based on our observation that the correlation between caries and the buffering capacity of the saliva in a material clinically exposed to fluoride is not linear as was previously thought. Rather least caries is developed in an intermediate buffering group that can be identified by our test method. We have also shown that the buffering changes over time and in the form of a test provide an aid in demonstrating the significance that a change assumes in the activity of the caries process.

REFERENCES 1. ten Cate J. M. & Duijsters P. P. E Influence of Fluorides in Solution on Tooth Demineralization , Caries Res 1983; 17: 193–9

2. Ekstrand J, Afseth J. Rölla G. Remineralisation. One of fluoride's most important cariostatic mechanisms. tandläk 1984; 20: 1123–1128

3. Jensen M. E. Responses of interproximal plaque pH to snack foods and effect of chewing sorbitol-containing gum. J A D A 1986; 113: 262–6.

4. Meurman J. Tooth Erosion. Näringsforskning 1987; 31: 146–9.

5. Modéer T. Tvetman S. Bergstrand F. et al. 3 year study of the effect of a fluoride varnish (Duraphat) on proximal caries progression in teenagers. Scan J Dent Res 1984; 92: 400–7.

What is claimed is:

1. An educational system for identifying tooth surface pH and determining optimal corresponding toothpaste pH, the system comprising:

a measuring device configured for insertion between two teeth, the measuring device providing a color indicator of pH;

a first fluoride toothpaste having a pH of about 8;

a second fluoride toothpaste having a pH of about 5; and a third fluoride toothpaste having a pH of about 4;

wherein one of the first, second and third fluoride toothpastes is selected in response to the measured tooth surface pH and is selected in order to bring the tooth surface pH to an optimal level for producing fluorapatite.

2. The educational system of claim 1, wherein the tooth surface pH corresponding to the optimal level for producing fluorapatite is in the range of about 4.5 to 5.5.

3. The educational system of claim 1, wherein the tooth surface pH is measured about 20 minutes after the tooth surface has been exposed to sugar.

4. The educational system of claim 1, wherein the measuring device comprises a reagent portion.

5. The educational system of claim 4, wherein the reagent portion has a straight side and a curved side, the curved side being similar to a toboggan run.

6. The educational system of claim 4, wherein the reagent portion comprises a desiccated 0.09 percent alcohol solution of bromocresol blue and bromothyl blue.

7. The educational system of claim 4, wherein the reagent portion becomes yellow if the tooth surface pH is too low, remains green if the tooth surface pH is optimal, and becomes blue if the tooth surface pH is too high.

8. The educational system of claim 7, wherein the reagent portion remains green to indicate a tooth surface pH between about 4.5 and 5.5, turns yellow to indicate a tooth surface pH below about 4.5 and turns blue to indicate a tooth surface pH above about 5.5.

9. The educational system of claim 7, wherein the first fluoride toothpaste having a pH of about 8 has a yellow color marking to indicate its intended use when the reagent portion turns yellow; the second fluoride toothpaste having a pH of about 5 has a green color marking to indicate its intended use when the reagent portion remains green; and the third fluoride toothpaste having a pH of about 4 has a blue color marking to indicate its intended use when the reagent portion turns blue.

10. The educational system of claim 9, wherein the yellow marked toothpaste can raise the tooth surface pH from about 4 to a pH between about 4.5 and 5.5; the green marked toothpaste can prolong a time interval in which the tooth surface pH remains between about 4.5 and 5.5; and the blue marked toothpaste can reduce the tooth surface pH from about 7 to a pH between about 4.5 and 5.5.

11. The educational system of claim 9, wherein the yellow marked toothpaste comprises about 15–22 percent of bicarbonate; the green marked toothpaste and the blue marked toothpaste both comprise about 0.3 to 0.9 percent citric acid.

12. A method for identifying tooth surface pH and determining optimal corresponding toothpaste pH, the method comprising steps of:

contacting the tooth surface with sugar;

contacting the tooth surface with a measuring device that provides a color indication of pH;

matching the tooth surface pH with a fluoride toothpaste that is selected in order to bring the tooth surface pH to an optimal level for producing fluorapatite.

13. The method of claim 12, wherein the step of selecting a fluoride toothpaste comprises selecting from a first fluoride toothpaste having a pH of about 8; a second fluoride toothpaste having a pH of about 5; and a third fluoride toothpaste having a pH of about 4.

14. The method of claim 12, wherein the tooth surface pH corresponding to the optimal level for producing fluorapatite is in the range of about 4.5 to 5.5.

15. The method of claim 12, wherein the step of measuring the tooth surface pH is conducted about 20 minutes after the tooth surface has been exposed to sugar.

16. The method of claim 12, wherein the measuring device comprises a reagent portion that becomes yellow if the tooth surface pH is too low, remains green if the tooth surface pH is optimal, and becomes blue if the tooth surface pH is too high.

17. The method of claim 16, wherein the reagent portion remains green to indicate a tooth surface pH between about 4.5 and 5.5, turns yellow to indicate a tooth surface pH below about 4.5 and turns blue to indicate a tooth surface pH above about 5.5.

18. The method of claim 16, wherein the first fluoride toothpaste having a pH of about 8 has a yellow color marking to indicate its intended use when the reagent portion turns yellow; the second fluoride toothpaste having a pH of about 5 has a green color marking to indicate its intended use when the reagent portion remains green; and the third fluoride toothpaste having a pH of about 4 has a blue color marking to indicate its intended use when the reagent portion turns blue.

* * * * *